United States Patent [19]
Takizawa et al.

[11] 4,297,369
[45] Oct. 27, 1981

[54] CERTAIN MUSCLE RELAXANT 3-METHYL-2-BENZOFURAN ACETAMIDES

[75] Inventors: Hiroshi Takizawa, Shizuoka; Yutaka Enomoto, Sakai; Yoshimasa Oiji, Shizuoka; Tatsuyuki Hirayama, Shizuoka; Tamotu Hashimoto, Shizuoka, all of Japan

[73] Assignee: Kyowa Hakko Kogyo Co., Ltd., Tokyo, Japan

[21] Appl. No.: 172,949

[22] Filed: Jul. 28, 1980

[30] Foreign Application Priority Data

Jul. 26, 1979 [JP] Japan ................................. 54-94180
Mar. 12, 1980 [JP] Japan ................................. 55-30312

[51] Int. Cl.$^3$ ...................... A61K 31/34; C07D 307/54
[52] U.S. Cl. ................................. 424/285; 260/346.73
[58] Field of Search .................... 260/346.73; 424/285

[56] References Cited

U.S. PATENT DOCUMENTS 4,126,625 11/1978 Yoshina et al. ................ 260/346.22

FOREIGN PATENT DOCUMENTS 1199781 9/1965 Fed. Rep. of Germany .
1025563 4/1965 United Kingdom .

OTHER PUBLICATIONS

Chem. Abstracts, vol. 34, No. 3 (1940), 757–758.
Chem. Abstracts, vol. 60, No. 1 (1964), 486d.

Primary Examiner—Henry R. Jiles
Assistant Examiner—Bernard Dentz
Attorney, Agent, or Firm—Craig and Antonelli

[57] ABSTRACT

The present invention relates to certain novel benzo[b]furan derivatives, namely, 5-substituted-2-substituted carbamoylmethyl-3-methyl benzo[b]furan having interesting pharmacological properties, in particular a muscle relaxant activity.

8 Claims, No Drawings

CERTAIN MUSCLE RELAXANT 3-METHYL-2-BENZOFURAN ACETAMIDES

BACKGROUND OF THE INVENTION

The compound represented by the formula (II')

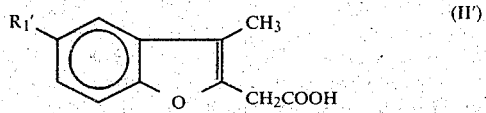

wherein $R_1'$ represents a hydrogen atom; an alkyl group; an alkoxy group; a cycloalkyl group; a cycloalkoxy group; an alkenyl group; an alkenyloxy group; a cyclohexenyloxy group; a phenyl group; a substituted phenyl group; a benzyl group; a substituted benzyl group; a trifluoromethyl group; or a halogen atom, [hereinafter referred to as the compound (II')] having an antiphlogistic and analgesic activity is disclosed in U.S. Pat. No. 4,126,625.

As a result of various studies, the present inventors have found that certain novel 2-substituted-carbamoyl-methyl-3-methyl-5-substituted derivatives of benzo[b]furan prepared from the compound (II') have a strong muscle relaxant activity.

DETAILED DESCRIPTION OF THE INVENTION

This invention relates to novel benzo[b]furan derivatives represented by the general formula (I):

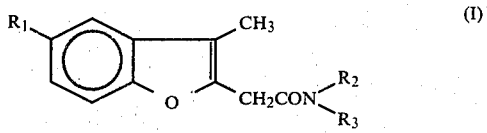

(wherein $R_1$ represents an alkyl group having 1-4 carbon atoms, an alkoxy group having 1-4 carbon atoms, a phenyl group or a halogen atom, $R_2$ and $R_3$ may be the same or different and represent a hydrogen atom or an alkyl group having 1-4 carbon atoms wherein, when one of $R_2$ and $R_3$ represents a hydrogen atom, the other represents an alkyl group), and a muscle relaxant pharmaceutical preparation containing as the active ingredient, the compound represented by the general formula (I) [hereinafter referred to as compound (I)].

The inventors have found for the first time that compounds (I), are useful compounds showing a muscle relaxant activity, anticonvulsant activity, antiinflammatory activity, and analgesic activity.

Inventors have also found that 5-substituted-2-(N,N-dimethylcarbamoyl)methyl-3-methylbenzo[b]furan has a strong muscle relaxant activity, anticonvulsant activity, antiinflammatory activity and analgesic activity.

The compounds (I) can be prepared from the compounds represented by the formula (II):

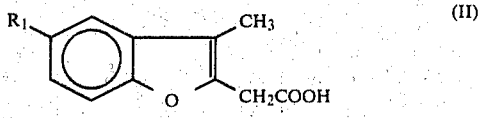

(wherein $R_1$ has the same meaning as defined above) [hereinafter referred to as compound (II)] according to various processes. The compound (II) is disclosed in U.S. Pat. No. 4,126,625, and Japanese Unexamined patent application Nos. 10256/77, 10257/77, 10258/77, 10259/77, 10260/77 and 26326/78 etc.

Five typical processes for preparing the compounds (I) from the compounds (II) are described below.

(A) a process using an acid halide of the compound (II) and an amine represented by the formula (III):

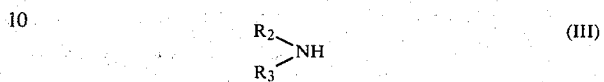

(wherein $R_2$ and $R_3$ have the same meaning as defined above) [hereinafter referred to as compound (III)]. The reaction is illustrated by the following reaction formula:

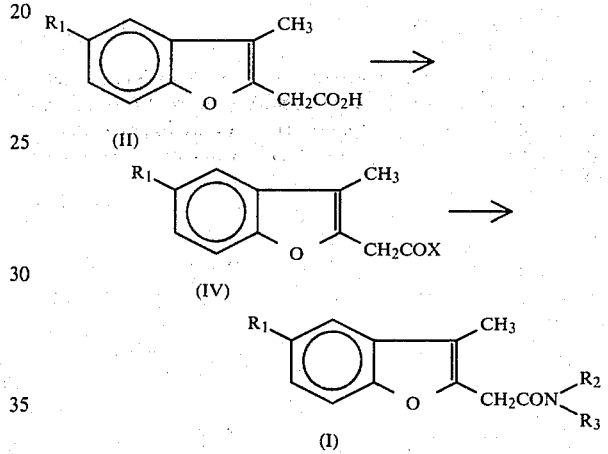

(B) a direct condensation process of the compound (II) with the compound (III) in the presence of a coupling agent.

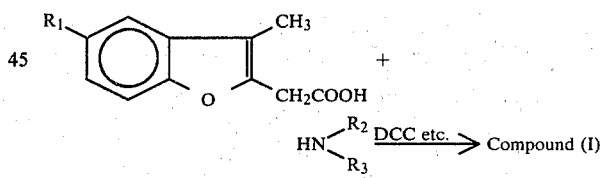

(C) a condensation process of an active ester of compound (II) with the compound (III).

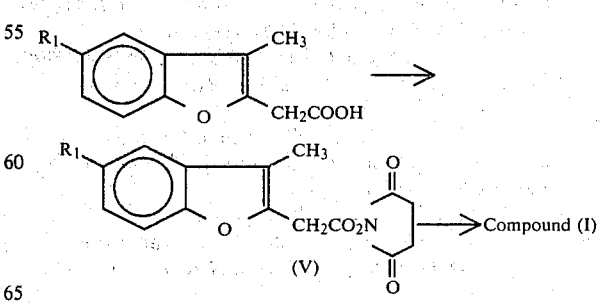

(D) a condensation process of a mixed acid anhydride of compound (II) with the compound (III).

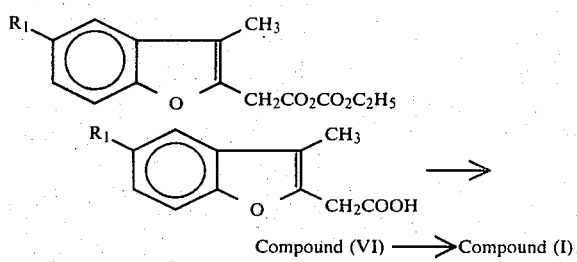

Compound (VI) ⟶ Compound (I)

(E) a process using an azide of compound (II)

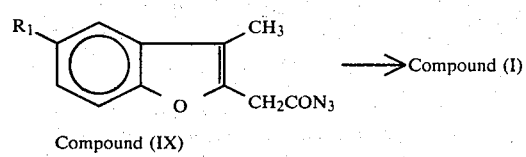

Compound (IX)

This acid azide is prepared from an acid halide (see Process A), an acid hydrazide directly derived from the compound (II), or prepared from an acid hydrazide derived from the compound (II) via an ester derivative thereof.

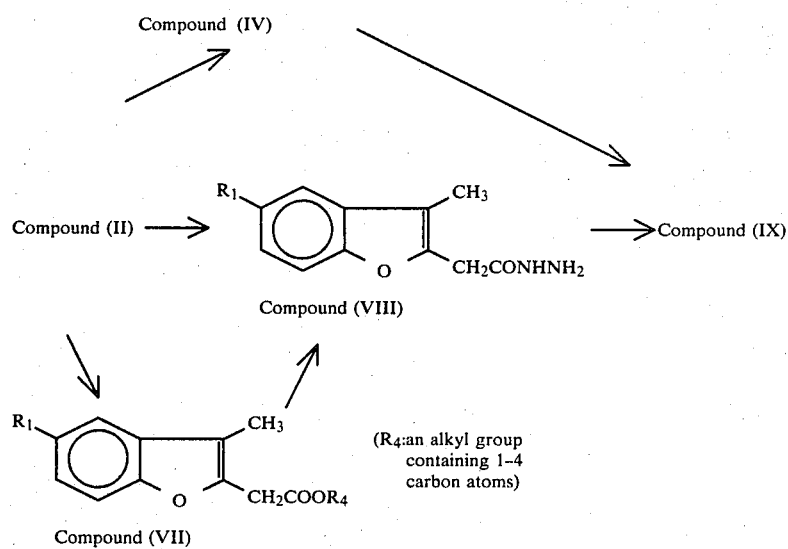

($R_4$: an alkyl group containing 1–4 carbon atoms)

Further, as processes for preparing the compound (I) without amines, there are illustrated various processes. For example, as a process for preparing the compound (I) wherein both $R_2$ and $R_3$ represent a methyl group, there are illustrated the following processes:

a process using a hexamethylphosphoramide solution (Process F) [reference: Chem. Ind. (London), 1966, 1529];

a process using a dimethylformamide solution of phosphorus pentoxide (Process G) [reference: Monatsh Chem, 99, 1799 (1968)];

a process using an alkali salt of compound (II) and dimethylcarbamoyl chloride to decarboxylate (Process H) [reference: J. Org. Chem., 28, 232 (1963)];

and a process using the acid halide of the compound (II) and N,N-dimethylformamide (Process J) [reference: J. Amer. Chem. Soc., 76, 1372 (1954)].

The desired compound (I) can be easily obtained by any of these processes. The processes will be exemplified in the following Examples.

It is possible to obtain other proper compounds having desired $R_2$ and $R_3$, by using suitable reagents according to a similar process to the above-mentioned processes.

Processes A–E are described in more detail below.
Process A:

The compound (II) is reacted with an inorganic halogen compound to obtain the compound represented by the formula (IV) [hereinafter referred to as compound IV]. This reaction may be conducted in the absence of a solvent, or may be conducted in a suitable inert solvent such as methylene chloride, chloroform, carbon tetrachloride, benzene, toluene, xylene, ethyl ether, isopropyl ether, tetrahydrofuran, pyridine, or triethylamine. In general, this reaction does not require particular catalysts, but the reaction can be accelerated by adding zinc chloride, pyridine, iodine, triethylamine, etc. in a catalytic amount to an equimolar amount. The reaction is carried out at room temperature to a boiling point of an inorganic halogen compound or a solvent used, and is completed in 30 minutes to 5 hours.

Amidation of the compound (IV) is conducted by adding an amine represented by the formula:

[hereinafter referred to as amine] to the solution containing the compound (IV) dissolved in an inert solvent as set forth hereinbefore. The amine is added in a gaseous or liquid form, or in a form dissolved in water or an inert solvent.

The amine is desirably used in an amount of 2 mols or more per mol of the compound (IV) so as to remove hydrohalogenic acid to be produced as a by-product. Otherwise, a tertiary amine like triethylamine is allowed to coexist, or pyridine or the like is used as a solvent. This reaction proceeds smoothly, and it is preferable to carry out the reaction at temperatures between −30° C. and room temperature so that the reaction solution would not be overheated owing to heat of the reaction.

The reaction is usually completed within time enough for the addition of the amine.

Process B:

According to this process, the reaction between the compound (II) and the amine is carried out using a coupling agent such as dicyclohexylcarbodiimide (hereinafter referred to as DCC) in an equimolar amount based on the compound (II). DCC can be used in an amount of 2–5 mols per mol of the compound (II) for accelerating the reaction and depressing formation of a by-product of acylurea. In this case, excess DCC may be decomposed with acetic acid after the reaction.

The reaction of compound (II) with the amine in equimolar amount is usually carried out in the solvent such as methylene chloride, chloroform, carbon tetrachloride, benzene, toluene, xylene, ethyl ether, isopropyl ether, tetrahydrofuran, dioxane, acetonitrile, ethyl acetate, dimethylformamide or the like in the presence of an equimolar amount of DCC.

The reaction is conducted at a temperature between −20° C. and 30° C. for 30 minutes to 5 hours. If necessary, it is further continued for 2 hours–20 hours at room temperature. If it is difficult to add the gaseous or liquid amine in an accurately equimolar amount based on the compound (II), the compound (II) and DCC are, in advance, reacted with each other in the aforesaid solvent, followed by adding thereto the amine to obtain the desired compound (I) in good yield. When the reactants are carried out in this order, an aqueous amine solution can be used and, when the used solvent is water-immiscible, it is desirable to stir the mixture as vigorously as possible. After completion of the reaction, dicyclohexylurea (hereinafter referred to as DCU) produced from DCC as by-product can be removed by filtration owing to its poor solubility in the aforesaid solvent. When DCU is not sufficiently recovered, the solvent used is once distilled off from the reaction solution to replace it by another poorer solvent for DCU such as methylene chloride or ethyl acetate. Then the remaining DCU is more sufficiently recovered by filtration. And, in the case of using carbonyldiimidazole (hereinafter referred to as CDI) as a coupling agent in place of DCC, the reaction can be conducted in the almost same manner as described above. The solvent for the reaction is required to be anhydrous, but only carbon dioxide and imidazole are formed as by-products during the reaction; the former can be allowed to escape because it is a gas, and the latter can be easily removed out of the reaction system by washing with an acidic water.

Process C:

An active ester compound represented by the general formula (V) [hereinafter referred to as compound (V)] can be obtained by reacting the compound (II) with an equimolar amount of N-hydroxysuccinimide (hereinafter referred to as NOS) in the presence of an equimolar amount of DCC in the same solvent as used in Process B. The reaction is conducted at −25° C. to room temperature for 30 minutes to 3 hours. If necessary, the reaction may be further continued for 3–20 hours. DCU precipitate formed is removed by filtration in the same manner as used in Process B to obtain a solution containing the compound (V). If desired, the solvent may be distilled off to obtain the crude compound (V) as an oil or crystals. Purification of the compound (V) may be carried out by the procedure of chromatography or recrystallization. Practically, the crude compound (V) filtrate per se obtained by removing DCU by filtration can be used for the subsequent reaction. That is, the compound (I) can be obtained by the reaction of the compound (V) with the amine. The used amine is added, in the same manner as described in Processes A and B, to the resulting solution containing compound (V) obtained as described above. The reaction is conducted at −25° C. up to room temperature for 30 minutes to 3 hours, and, if necessary, the reaction is further continued for 2–20 hours. By-product from the compound (V), that is, NOS can easily be removed, after the reaction, by washing the reaction solution with a sodium bicarbonate aqueous solution owing to its high solubility of NOS in water. In a similar manner to that described above, there can be obtained other active ester compounds by using hydroxy group-containing reagents such as p-nitrophenol, 2,4,5-trichlorophenol, N-hydroxyphthalimide, etc. The reaction of these active ester compounds with the amine can be carried out in the same manner as that of the compound (V) to obtain the compound (I).

Process D:

A mixed acid anhydride represented by the general formula (VI) [hereinafter referred to as compound (VI)] is obtained by reacting the compound (II) with an equimolar amount of ethyl chlorocarbonate in the presence of an equimolar amount of a base such as triethylamine, tri-n-butylamine or N-methylmorpholine in an inert solvent. As the solvent, the same anhydrous ones as used in Process B are used. The reaction is preferably conducted at a temperature between −20° C. and 15° C., and is usually completed in time enough for the addition of ethyl chlorocarbonate. The reaction solution per se can be used for the subsequent reaction without isolating the thus obtained compound (VI). Compound (I) is obtained by adding the amine to the above-prepared solution at the same temperature. The reaction is usually conducted for 30 minutes to 2 hours, and if necessary, the reaction may be further continued. The use of a mixed acid anhydride obtained from the compound (II) and a monoalkyl chlorocarbonate (e.g., butyl chlorocarbonate), an organic acid chloride (e.g., isovaleryl chloride or pivaloyl chloride) or an inorganic acid (e.g., phosphorus oxychloride or sulfuric anhydride) also provides the compound (I).

Process E:

(1) The starting material of an acid azide compound represented by the general formula (IX) [hereinafter referred to as compound (IX)] is obtained by reacting the compound (IV) prepared in Process A with sodium azide. In this reaction, sodium azide is used in an amount of 1.1–1.5 mols per mol of the compound (IV). As the reaction solvent, there may be used inert solvents such as ethyl ether, isopropyl ether, benzene, toluene, xylene, nitrobenzene, ethanol, isopropanol, acetone, methyl ethyl ketone, dioxane, tetrahydrofuran, etc. alone or in combination and, if necessary, a minimum amount of water is added thereto for dissolving sodium azide. The reaction is conducted at −5° C. to 15° C. for 30 minutes to 2 hours. If necessary, the reaction is further continued for 30 minutes to 2 hours. Usually, compound (IV) is added to a solution containing sodium azide with stirring. After completion of the reaction, ice-water is added to the reaction solution to precipitate compound (IX) or to transfer the compound to an organic solvent layer, thus the compound (IX) being separated off.

(2) Compound (IX) is also obtained by reacting an acid hydrazide compound represented by the general formula (VIII) [hereinafter referred to as compound (VIII)] with nitrous acid. The compound (VIII) is dissolved in hydrochloric acid or acetic acid aqueous solution containing 1–1.1 mols per mol of the compound (VIII), and a cold aqueous sodium nitrite solution containing 1–1.2 mols per mol of the compound (VIII), of sodium nitrite is slowly added to said solution with stirring. After completion of the addition, the reaction may, if necessary, be further continued for 30 minutes–2 hours. Thus, compound (IX) is obtained as crystals. If necessary, the reaction is conducted in the presence of a water-insoluble organic solvent such as ethyl ether to transfer easily the compound (IX) to the organic solvent layer.

Additionally, the compound (VIII) is obtained by reacting the compound (II) with hydrazine in the presence of DCC in the same manner as described in Process B.

In general, the compound (VIII) is obtained by reacting an ester derivative represented by the general formula (VII) [hereinafter referred to as compound (VII)] in an aqueous solution containing 1–10 mols of hydrazine hydrate per mol of the compound (VII) at room temperature to 100° C. for 30 minutes to 10 hours. Further, compound (VII) is also obtained by heating the compound (II) in an alcohol in the presence of a catalytic amount of acid (e.g., sulfuric acid, hydrochloric acid, p-toluenesulfonic acid, etc.).

(3) The thus obtained compound (IX) is reacted with the amine in an amount of 1–10 mols per mol of the compound (IX) for 5–48 hours to obtain the desired product. The reaction is preferably conducted at $-10°$ C. to 10° C., and the amine may be added in a gaseous form or in a form of the solution dissolved in a suitable solvent.

When the compound (IX) is obtained as a solution as described in the above (1) and (2), it may be used per se.

Isolation of the compound (I) thus obtained is conducted in a conventional manner employed in organic chemistry. Preferably, the compound (I) is subjected to column chromatography or recrystallization. As the specific examples of the compounds provided by the present invention, there are illustrated those wherein $R_1$ represents a methyl group, an ethyl group, an n-propyl group, an i-propyl group, an n-butyl group, a sec-butyl group, a tert-butyl group, an iso-butyl group, a methoxy group, an ethoxy group, an n-propoxy group, an i-propoxy group, an n-butoxy group, a sec-butoxy group, a tert-butoxy group, an iso-butoxy group, a phenyl group, a chlorine atom, a bromine atom, a fluorine atom or an iodine atom, and each of $R_2$ and $R_3$ represents a hydrogen atom, a methyl group, an ethyl group, an n-propyl group, an i-propyl group, an n-butyl group, a sec-butyl group, a tert-butyl group or an iso-butyl group.

As is demonstrated in Examples mentioned below hereinafter, the compounds provided by the present invention are useful compounds having strong muscle-relaxant activity, anticonvulsant activity, and anti-inflammatory and analgesic activity with less toxicity. As medicines, they are to be usually administered in an amount of 200–600 mg per day per adult either in one dose or in two or three doses. They are administered in the form of tablets, granules, powder, capsules, syrup, ointment, cream, injection, or the like prepared in a conventional manner depending upon the purpose and method of the administration. For example, in a tablet form, tablets containing 50–150 mg active ingredient per tablet are preferably used. In preparing tablets, an excipient (e.g., lactose, glucose, sucrose, mannitol, etc.), a disintegrator (e.g., starch, sodium alginate, carboxymethyl cellulose calcium, crystalline cellulose, etc.), a lubricant (e.g., magnesium stearate, talc, etc.), a binder (e.g., hydroxypropylcellulose, gelatin, polyvinyl alcohol, polyvinyl pyrrolidone, etc.), a surfactant (e.g., sucrose fatty acid ester, sorbitan fatty acid ester, etc.), a plasticizer (e.g., glycerin, etc.), and the like are used in a conventional manner.

Certain specific embodiments of the invention are illustrated by the following representative examples.

EXAMPLE 1

Preparation of 2-dimethylcarbamoylmethyl-3-methyl-5 methoxybenzo[b]furan [hereinafter referred to as compound (A)]:

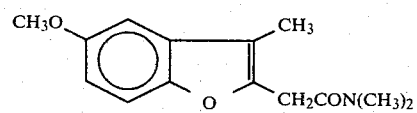

In this example, 11.1 g of 3-methyl-5-methoxybenzo[b]furyl-2-acetic acid is refluxed for 1 hour in 20 ml of thionyl chloride. After completion of the reaction, thionyl chloride is distilled off under reduced pressure, the residue is dissolved in 20 ml of ethyl ether, and the resulting solution is added dropwise to 50 ml of a 20% aqueous solution of dimethylamine in one hour with ice-cooling. After completion of the dropwise addition, the reaction solution is extracted with 100 ml of chloroform, and the extract is dehydrated, followed by distilling off chloroform under reduced pressure. The residue is subjected to silica gel column chromatography. Elution is carried out using a cyclohexane-diethylamine mixture (1:1 by volume). Concentration of the main fractions under reduced pressure gives 7.0 g of crude crystals in a 57% yield. Recrystallization of the product from 200 ml of n-hexane gives 4.3 g of purified crystals in a recrystallization yield of 61%. The product has the following properties, thus being identified as the desired compound of 2-dimethylcarbamoylmethyl-3-methyl-5-methoxybenzo[b]furan.

Melting point: 78°–79° C.

IR spectrum (KBr tablet, cm$^{-1}$): 2910, 1645, 1480, 1390, 1205, 820.

NMR spectrum (CDCl$_3$, δ value, ppm): 2.13(s, 3H), 2.89 (s, 3H), 2.97(s, 3H), 3.72(s, 2H), 3.75(s, 3H), 6.63–7.40(m, 3H).

Elemental analysis for $C_{14}H_{17}NO_3$:

|  | C (%) | H (%) | N (%) |
| --- | --- | --- | --- |
| Calculated: | 67.99 | 6.93 | 5.66 |
| Found: | 67.84 | 7.23 | 5.80 |

This process is one of typical embodiments of Process A.

EXAMPLE 2

Preparation of 2-dimethylcarbamoylmethyl-3,5-dimethylbenzo[b]furan [hereinafter referred to as compound (B)]:

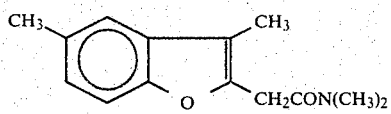

In this example, 10.0 g of 3,5-dimethylbenzo[b]furyl-2-acetic acid and 5.7 g of N-hydroxysuccinimide are dissolved in 200 ml of tetrahydrofuran, and 10.5 g of dicyclohexylcarbodiimide is added thereto with ice-cooling, then stirred for 5 hours. The reaction solution is concentrated under reduced pressure to distill off tetrahydrofuran, and 150 ml of ethyl acetate is added thereto to remove insoluble crystals by filtration. The filtrate is added dropwise to 100 ml of a 20% aqueous solution of dimethylamine for 30 minutes with vigorously stirring under ice-cooling. After completion of the reaction, the aqueous layer is separated off, and the ethyl acetate solution is dehydrated and concentrated under reduced pressure to obtain 7.0 g of crude crystals in a 62% yield. Recrystallization of the crude product from 150 ml of n-hexane gives 6.0 g of purified crystals in a 86% recrystallization yield. This compound has the following properties, thus being identified as the desired product of 2-dimethylcarbamoylmethyl-3,5-dimethylbenzo[b]furan.

Melting point: 101°–103° C.

IR spectrum (KBr tablet, cm$^{-1}$): 2910, 1645, 1460, 1390, 1145, 800.

NMR spectrum (CDCl$_3$, δ value, ppm): 2.18(s, 3H), 2.41 (s, 3H), 2.95(s, 3H), 3.06(s, 3H), 3.79(s, 2H), 6.85–7.42(m, 3H)

Elemental analysis for C$_{14}$H$_{17}$NO$_2$:

|  | C (%) | H (%) | N (%) |
|---|---|---|---|
| Calculated: | 72.63 | 7.49 | 6.22 |
| Found: | 72.70 | 7.41 | 6.06 |

This process is one of typical embodiments of Process C.

EXAMPLE 3

Preparation of 2-dimethylcarbamoylmethyl-3-methyl-5-phenylbenzo[b]furan [hereinafter referred to as compound (C)]:

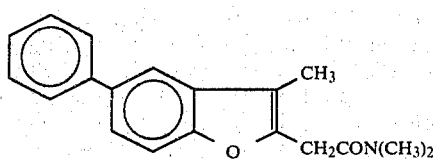

In this example, 20 ml of methanol and 3.6 g of a 28% methanol solution of sodium methylate are added to 5.0 g of 3-methyl-5-phenylbenzo[b]furyl-2-acetic acid, then concentrated under reduced pressure to dryness. 2.0 g of dimethylcarbamoyl chloride is added thereto, and the resulting mixture is heated for 3 hours at 100° C., then for 10 minutes at 150° C. After completion of the reaction, 50 ml of chloroform is added thereto to reflux for 10 minutes. Then, hot chloroform solution decanted is concentrated under reduced pressure to obtain 5.1 g of crude crystals in a 92% yield. Recrystallization of this product from 150 ml of ligroin gives 4.2 g of purified crystals in a recrystallization yield of 82%. The compound has the following properties, thus being identified as the desired product of 2-dimethylcarbamoylmethyl-3-methyl-5-phenylbenzo[b]furan.

Melting point: 96.5°–98° C.

IR spectrum (KBr tablet, cm$^{-1}$): 2920, 1650, 1470, 1395, 1140, 780.

NMR spectrum (CDCl$_3$, δ value, ppm): 2.16(s, 3H), 2.84 (s, 3H), 2.89(s, 3H), 3.68(s, 2H), 7.10–7.73(m, 8H)

Elemental analysis for C$_{19}$H$_{19}$NO$_2$:

|  | C (%) | H (%) | N (%) |
|---|---|---|---|
| Calculated: | 77.79 | 6.53 | 4.77 |
| Found: | 78.18 | 6.52 | 4.60 |

This process is one of typical embodiments of Process H.

EXAMPLE 4

Preparation of 2-dimethylcarbamoylmethyl-3-methyl-5-fluorobenzo[b]furan [hereinafter referred to as compound (D)]:

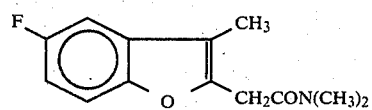

In this example, 5.0 g of 3-methyl-5-fluorobenzo[b]furyl-2-acetic acid is refluxed for 1 hour in 10 ml of thionyl chloride. After completion of the reaction, thionyl chloride is distilled off under reduced pressure, and 10 ml of dimethylformamide is added to the residue to reflux for 6 hours. 50 ml of water is added to the reaction solution and, after ice-cooling for one hour, crystals precipitated are collected by filtration to obtain 4.7 g of crude crystals in a 83% yield. Recrystallization of this product from 25 ml of a water-methanol (1:1 by volume) mixture gives 4.0 g of purified crystals in a 85% recrystallization yield. This product has the following properties, thus being identified as the desired product of 2-dimethylcarbamoylmethyl-3-methyl-5-fluorobenzo[b]furan.

Melting point: 88°–90° C.

IR spectrum (KBr tablet, cm$^{-1}$): 2910, 1645, 1460, 1390, 1175, 805.

NMR spectrum (CDCl$_3$, δ value, ppm): 2.13(s, 3H), 2.92 (s, 3H), 3.02(s, 3H), 3.76(s, 2H), 6.63–7.43(m, 3H).

Elemental analysis for C$_{13}$H$_{14}$NO$_2$F:

|  | C (%) | H (%) | N (%) | F (%) |
|---|---|---|---|---|
| Calculated: | 66.37 | 6.00 | 5.96 | 8.08 |
| Found: | 66.40 | 5.91 | 6.00 | 7.92 |

This process is one of typical embodiments of Process J.

EXAMPLE 5

Acute toxicity

Male dd mice weighing 19–21 g and male Wistar rats weighing 170–190 g were used in groups of 3–6 animals. The drugs were suspended in a 0.3% carboxymethyl cellulose solution and administered orally. The animals were observed for mortality and $LD_{50}$ values were determined from the number of dead animals for 7 days. As the reference compound, benzydamine.HCl was dissolved in water and administered orally. (In Example, 6, 7 and 8, the drugs and benzydamine. HCl were also administered in the same manner.

| Compound | $LD_{50}$ mg/Kg p.o. Mice | Rats |
|---|---|---|
| A | > 1000 | — |
| B | > 3000 | > 3000 |
| C | > 1000 | — |
| D | > 1000 | — |
| Benzydamine . HCl | 500–1000 | > 1500 |

EXAMPLE 6

Muscle relaxant activity

Groups of 5 male dd mice weighing 19–21 g were used. The mice which remained for a period of 3 min. on a 3 cm diameter rod rotating at 5 r.p.m. were selected and tested to determine the muscle relaxant activity at 1, 2 and 4 hr. after drug administration. The methods employed are as follows.

Slant test

Each mouse was mounted on a 45°-inclined wire netting to examine whether it fell off or not.

Traction test

Forefeet of each mouse were placed on a wire to examine whether it fell off or not.

Rotating rod test

Each mouse was mounted on a rotating rod to examine whether it fell off or not within 2 min.

In each test, the compound was considered to have the muscle relaxant activity when the mice fell off. The results thus obtained are tabulated below.

| Compound | Dose mg/kg, p.o. | No. of falling mice/five tested mice (given in the order of slant, traction and rotating rod test) Time after oral administration (hr) | | |
|---|---|---|---|---|
| | | 1 | 2 | 4 |
| A | 300 | 3, 2, 5 | 1.5, 2, 3 | 0, 0, 1 |
| B | 300 | 5, 5, 5 | 4, 5, 5 | 0, 0, 0 |
| C | 300 | 1.5, 2, 3 | 1.5, 3, 3 | 0, 0, 0 |
| D | 300 | 4.5, 5, 5 | 4.5, 5, 5 | 1, 1, 2 |
| Benzydamine hydrochloride | 200 | 2, 0, 4 | 1, 0, 2 | 0, 0, 0 |

EXAMPLE 7

Anticonvulsant activity

Anticonvulsant activity was determined according to the following three methods.

(1) Maximal electroshock convulsion test

Groups of 10 male dd mice weighing 22–24 g were used. The drugs were orally administered and one hr. later, the mice were subjected to an electric current (2000 V, 50 mA) for 0.2 sec. through corneal electrodes. Drug activity is expressed as the percent blocking tonic extensor seizures.

(2) Strychnine convulsion test

Groups of 10 male dd mice weighing 19–21 g were used. The drugs were orally administered and one hr. later, strychnine was injected subcutaneously at 2 mg/kg. Drug activity is expressed as the percent blocking tonic extensor seizures.

(3) Pentetrazol convulsion test

Groups of 10 male dd mice weighing 19–21 g were used. The drugs were orally administered and one hr. later, pentetrazol was injected subcutaneously at 120 mg/kg. Drug activity is expressed as the percent blocking clonic seizures.

The results of the above three studies are shown below.

| Compound | Maximal Electroshock Test | | Strychnine Convulsion Test | | Pentetrazole Convulsion Test | |
|---|---|---|---|---|---|---|
| | Dose mg/Kg, p.o. | % Inhibition | Dose mg/Kg, p.o. | % Inhibition | Dose mg/Kg, p.o. | % Inhibition |
| A | 100 | 30 | 300 | 60 | 150 | 40 |
| B | 100 | 80 | 300 | 88 | 150 | 90 |
| C | 100 | 100 | 300 | 70 | 150 | 30 |
| D | 100 | 85 | 300 | 57 | 150 | 80 |
| Benzydamine . HCl | 100 | 100 | 100 | 70 | 200 | 0 |

EXAMPLE 8

Anti-inflammatory activity and analgesic activity (1) Anti-inflammatory activity Groups of 5 male Wistar rats weighing 130–150 g were used. One hr. after drug administration, 0.1 ml of a 1% aqueous suspension of carrageenin was injected into the plantar surface of the right hind paw. The volume of the injected paw was measured before and 3 hr. after carrageenin injection by mercury displacement. Drug activity is expressed as the percent difference between the test and control groups' edema.

(2) Analgesic activity

Groups of 10 male dd mice weighing 19–21 g were used. One hr. after drug administration, 0.2 ml of a 0.7% aqueous solution of acetic acid was injected intraperitoneally. Ten min. after acetic acid injection, the number of writhes was counted for each mouse during the following 10 min. Drug activity is expressed as the percent inhibition of the number of writhes in the control group.

The results thus obtained are shown below.

| Compound | Anti-inflammatory Activity | | Analgesic Activity | |
|---|---|---|---|---|
| | Dose mg/Kg, p.o. | % Inhibition | Dose mg/Kg, p.o. | % Inhibition |
| A | 300 | 23.3 | 150 | 83.6 |

-continued

| Compound | Anti-inflammatory Activity | | Analgesic Activity | |
|---|---|---|---|---|
| | Dose mg/Kg, p.o. | % Inhibition | Dose mg/Kg, p.o. | % Inhibition |
| B | 300 | 10.2 | 150 | 24.0 |
| C | 300 | 20.4 | 150 | 48.4 |
| D | 300 | 31.2 | 150 | 32.9 |
| Benzydamine hydrochloride | 400 | 20.9 | 400 | 95.2 |

EXAMPLE 9

10,000 tablets were prepared in a conventional manner according to the following formulation. Each tablet contained 50 mg active ingredient.

| | |
|---|---|
| 2-Dimethylcarbamoylmethyl-3-methyl-5-methoxybenzo[b]furan | 500 g |
| Lactose | 343 g |
| Carboxymethyl cellulose calcium | 93 g |
| Magnesium stearate | 4 g |
| Talc | 8 g |
| Polyvinyl alcohol | 25 g |
| Methyl cellulose | 25 g |
| Glycerine | 2 g |
| Tar dye | trace |

EXAMPLE 10

A powder was prepared in a conventional manner according to the following formulation.

| | |
|---|---|
| 2-Dimethylcarbamoylmethyl-3,5-dimethylbenzo[b]furan | 150 g |
| D-Mannitol | 850 g |

EXAMPLE 11

Capsules having the following composition were prepared in a conventional manner.

| | |
|---|---|
| 2-Dimethylcarbamoyl-3-methyl-5-fluorobenzo[b]furan | 100 mg per capsule |
| Crystalline cellulose | 30 mg per capsule |
| Magnesium stearate | 3.6 mg per capsule |
| Talc | 3.6 mg per capsule |

EXAMPLE 12

Compounds (E)-(S) are prepared in the same manner as in Process A described in Example 1 except the starting materials given in Table 1 shown below, are used.

Preparation of 2-(methylcarbamoyl)methyl-3-methyl-5-fluorobenzo[b]furan [hereinafter referred to as compound (E)]:

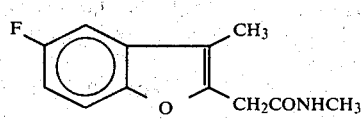

Melting point: 170°–172° C. (recrystallized from toluene)

IR spectrum (KBr tablet, cm$^{-1}$): 3280, 1645, 1570, 1465, 1165, 805.

NMR spectrum (CDCl$_3$, δ value, ppm): 2.17(s, 3H), 2.78 (d, 3H), 3.67(s, 2H), 5.80(broad, 1H), 6.60–7.60 (m, 3H).

Elemental analysis for C$_{12}$H$_{12}$NO$_2$F:

| | C (%) | H (%) | N (%) |
|---|---|---|---|
| Calculated: | 65.15 | 5.47 | 6.33 |
| Found: | 64.99 | 5.49 | 6.40 |

Preparation of 2-(ethylcarbamoyl)methyl-3-methyl-5-fluorobenzo[b]furan [hereinafter referred to as compound (F)]:

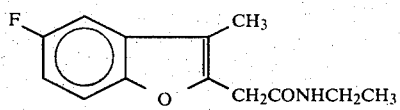

Melting point: 155°–158° C. (recrystallized from toluene)

IR spectrum (KBr tablet, cm$^{-1}$): 3270, 1645, 1570, 1465, 1190, 810.

NMR spectrum (CDCl$_3$, δ value, ppm): 1.10(t, 3H), 2.17 (s, 3H), 3.03–3.50(m, 2H), 3.65(s, 2H), 5.90 (broad, 1H), 6.67–7.50(m, 3H).

Elemental analysis for C$_{13}$H$_{14}$NO$_2$F:

| | C (%) | H (%) | N (%) |
|---|---|---|---|
| Calculated: | 66.37 | 6.00 | 5.96 |
| Found: | 66.42 | 6.10 | 6.01 |

Preparation of 2-(n-propylcarbamoyl)methyl-3-methyl-5-fluorobenzo[b]furan [hereinafter referred to as compound (G)]:

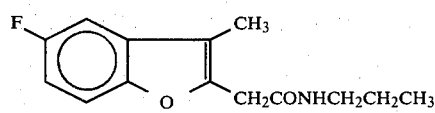

Melting point: 132°–134° C. (recrystallized from CCl$_4$)

IR spectrum (KBr tablet, cm$^{-1}$): 3280, 1645, 1555, 1475, 1190, 810.

NMR spectrum (CDCl$_3$, δ value, ppm): 0.87(t, 3H), 1.20–1.80(m, 2H), 2.17(s, 3H), 3.20(q, 2H), 3.65(s, 2H), 5.90(broad, 1H), 6.60–7.50(m, 3H).

Elemental analysis for C$_{14}$H$_{16}$NO$_2$F:

| | C (%) | H (%) | N (%) |
|---|---|---|---|
| Calculated: | 67.45 | 6.47 | 5.62 |
| Found: | 67.33 | 6.19 | 5.88 |

Preparation of 2-(sec-butylcarbamoyl)methyl-3-methyl-5-fluorobenzo[b]furan [hereinafter referred to as compound (H)]:

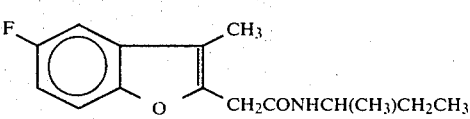

Melting point: 153°–155° C. (recrystallized from CCl₄)

IR spectrum (KBr tablet, cm⁻¹): 3280, 1645, 1550, 1460, 1170, 805.

NMR spectrum (CDCl₃, δ value, ppm): 0.83(t, 3H), 1.07 (d, 3H), 1.37(q, 2H), 2.17(s, 3H), 3.65(s, 2H), 3.60–4.20(m, 1H), 5.50(broad, 1H), 6.70–7.50(m, 3H).

Elemental analysis for $C_{15}H_{18}NO_2F$:

|  | C (%) | H (%) | N (%) |
| --- | --- | --- | --- |
| Calculated: | 68.42 | 6.89 | 5.32 |
| Found: | 68.31 | 7.01 | 5.09 |

Preparation of 2-(tert-butylcarbamoyl)methyl-3-methyl-5-fluorobenzo[b]furan [hereinafter referred to as compound (I)]:

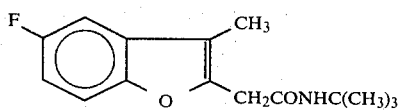

Melting point: 176°–179° C. (recrystallized from toluene)

IR spectrum (KBr tablet, cm⁻¹): 3280, 1650, 1565, 1470, 1365, 800.

NMR spectrum (CDCl₃, δ value, ppm): 1.32(s, 9H), 2.17 (s, 3H), 3.58(s, 2H), 5.60(broad, 1H), 6.70–7.50 (m, 3H).

Elemental analysis for $C_{15}H_{18}NO_2F$:

|  | C (%) | H (%) | N (%) |
| --- | --- | --- | --- |
| Calculated: | 68.42 | 6.89 | 5.32 |
| Found: | 68.28 | 6.77 | 5.21 |

Preparation of 2-(diethylcarbamoyl)methyl-3-methyl-5-fluorobenzo[b]furan [hereinafter referred to as compound (J)]:

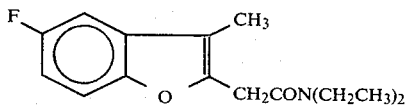

Melting point: 78°–80° C. (recrystallized from n-hexane)

IR spectrum (KBr tablet, cm⁻¹): 2970, 1640, 1460, 1255, 1160, 800.

NMR spectrum (CDCl₃, δ value, ppm): 1.13(t, 6H), 2.15 (s, 3H), 3.38(q, 4H), 3.75(s, 2H), 6.70–7.50(m, 3H)

Elemental analysis for $C_{15}H_{18}NO_2F$:

|  | C (%) | H (%) | N (%) |
| --- | --- | --- | --- |
| Calculated: | 68.42 | 6.89 | 5.32 |
| Found: | 68.44 | 7.00 | 5.09 |

Preparation of 2-(di-n-propylcarbamoyl)methyl-3-methyl-5-fluorobenzo[b]furan [hereinafter referred to as compound (K)]:

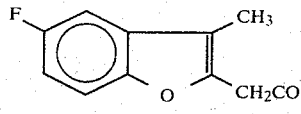

Melting point: 50°–53° C. (recrystallized from n-hexane)

IR spectrum (KBr tablet, cm⁻¹): 2960, 1645, 1470, 1165, 1085, 800.

NMR spectrum (CDCl₃, δ value, ppm): 0.90(t, 6H), 1.20–2.00(m, 4H), 2.15(s, 3H), 3.32(t, 4H), 3.78(s, 2H), 6.70–7.50(m, 3H).

Elemental analysis for $C_{17}H_{22}NO_2F$:

|  | C (%) | H (%) | N (%) |
| --- | --- | --- | --- |
| Calculated: | 70.08 | 7.61 | 4.81 |
| Found: | 69.87 | 7.39 | 5.02 |

Preparation of 2-(di-iso-propylcarbamoyl)methyl-3-methyl-5-fluorobenzo[b]furan [hereinafter referred to as compound (L)]:

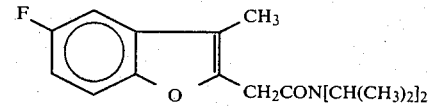

Melting point: 99°–102° C. (recrystallized from n-hexane)

IR spectrum (KBr tablet, cm⁻¹): 2970, 1630, 1450, 1335, 1175, 810.

NMR spectrum (CCl₄, δ value, ppm): 1.22(broad, 12H), 2.15(s, 3H), 3.65(s, 2H), 3.00–4.50(broad, 2H), 6.60–7.40(m, 3H)

Elemental analysis for $C_{17}H_{22}NO_2F$:

|  | C (%) | H (%) | N (%) |
| --- | --- | --- | --- |
| Calculated: | 70.08 | 7.61 | 4.81 |
| Found: | 70.05 | 7.56 | 5.10 |

Preparation of 2-(di-n-butylcarbamoyl)methyl-3-methyl-5-fluorobenzo[b]furan [hereinafter referred to as compound (M)]:

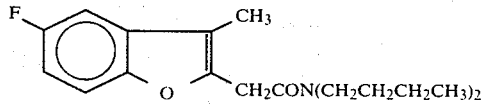

The compound is in the form of oil at room temperature.

IR spectrum (NaCl cell, cm⁻¹): 2960, 1650, 1460, 1250, 1185, 805.

NMR spectrum (CDCl₃, δ value, ppm): 0.50–1.90(m, 14H), 2.12(s, 3H), 3.30(t, 4H), 3.73(s, 2H), 6.60–7.40 (m, 3H).

Elemental analysis for $C_{19}H_{26}NO_2F$:

|  | C (%) | H (%) | N (%) |
| --- | --- | --- | --- |
| Calculated: | 71.44 | 8.20 | 4.38 |
| Found: | 71.43 | 8.11 | 4.42 |

Preparation of 2-(di-iso-butylcarbamoyl)methyl-3-methyl-5-fluorobenzo[b]furan [hereinafter referred to as compound (N)]:

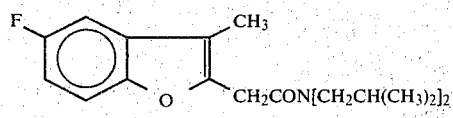

Melting point: 58°–60° C. (recrystallized from n-hexane)

IR spectrum (KBr tablet, cm$^{-1}$): 2960, 1645, 1465, 1230, 1175, 800.

NMR spectrum (CCl$_4$, δ value, ppm): 0.78, 0.88 & 0.98 (three peaks, 12H), 1.50–2.30(m, 2H), 2.12(s, 3H), 3.13(d, 4H), 3.67(s, 2H), 6.60–7.40(m, 3H)

Elemental analysis for $C_{19}H_{26}NO_2F$:

|  | C (%) | H (%) | N (%) |
|---|---|---|---|
| Calculated: | 71.44 | 8.20 | 4.38 |
| Found: | 71.57 | 8.31 | 4.39 |

Preparation of 2-(N-methyl-N-n-butyl)carbamoylmethyl-3-methyl-5-fluorobenzo[b]furan [hereinafter referred to as compound (O)]:

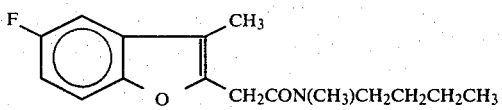

The compound is in the form of oil at room temperature.

IR spectrum (NaCl cell, cm$^{-1}$): 2930, 1650, 1460, 1250, 1170, 805.

NMR spectrum (CCl$_4$ δ value, ppm): 0.60–1.80(m, 7H), 2.10(s, 3H), 2.82 & 2.95(two peaks, 3H), 3.27(t, 2H), 3.65(s, 2H), 6.60–7.40(m, 3H)

Elemental analysis for $C_{16}H_{20}NO_2F$:

|  | C (%) | H (%) | N (%) |
|---|---|---|---|
| Calculated: | 69.29 | 7.27 | 5.05 |
| Found: | 69.14 | 6.98 | 4.96 |

Preparation of 2-(iso-propylcarbamoyl)methyl-3-methyl-5-fluorobenzo[b]furan [hereinafter referred to as compound (P)]:

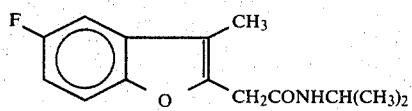

Melting Point: 175°–176° C. (recrystallized from benzenemethanol)

IR spectrum (KBr tablet, cm$^{-1}$): 3300, 2980, 2840, 1655, 1370, 1225.

NMR spectrum (CDCl$_3$, δ value, ppm): 1.11(d, 6H), 2.16 (s, 3H), 3.63(s, 2H), 3.70–4.30(m, 1H), 5.60(broad, 1H), 6.70–7.50(m, 3H).

Elemental analysis for $C_{14}H_{16}NO_2F$:

|  | C (%) | H (%) | N (%) |
|---|---|---|---|
| Calculated: | 67.45 | 6.47 | 5.62 |
| Found: | 67.63 | 6.48 | 5.53 |

Preparation of 2-(iso-propylcarbamoyl)methyl-3-methyl-5-methoxybenzo[b]furan [hereinafter referred to as compound (Q)]:

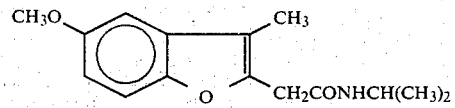

Melting point: 151°–152° C. (recrystallized from ethyl acetate).

IR spectrum (KBr tablet, cm$^{-1}$): 3300, 2980, 2840, 1655, 1370, 1225.

NMR spectrum (CDCl$_3$, δ value, ppm): 1.10(d, 6H), 2.16 (s, 3H), 3.62(s, 2H), 3.82(s, 3H), 3.70–4.30(m, 1H), 5.70(broad, 1H), 6.70–7.40(m, 3H).

Elemental analysis for $C_{15}H_{19}NO_3$:

|  | C (%) | H (%) | N (%) |
|---|---|---|---|
| Calculated: | 68.94 | 7.33 | 5.36 |
| Found: | 68.69 | 7.58 | 5.50 |

Preparation of 2-(iso-propylcarbamoyl)methyl-3-methyl-5-phenylbenzo[b]furan [hereinafter referred to as compound (R)]:

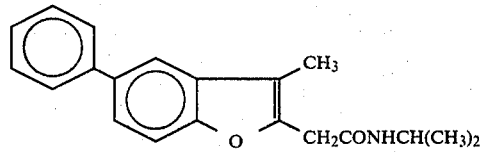

Melting point: 197°–198° C. (recrystallized from ethyl acetate)

IR spectrum (KBr tablet, cm$^{-1}$): 3310, 2975, 1645, 1460, 1350, 1210.

NMR spectrum (CDCl$_3$, δ value, ppm): 1.10(d, 6H,) 2.25 (s, 3H), 3.67(s, 2H), 3.70–4.30(m, 1H), 5.60 (broad, 1H), 7.20–7.80(m, 8H).

Elemental analysis for $C_{20}H_{21}NO_2$:

|  | C (%) | H (%) | N (%) |
|---|---|---|---|
| Calculated: | 78.14 | 6.89 | 4.56 |
| Found: | 77.57 | 6.98 | 4.73 |

Preparation of 2-(iso-propylcarbamoyl)methyl-3,5-dimethylbenzo[b]furan [hereinafter referred to as compound (S)]:

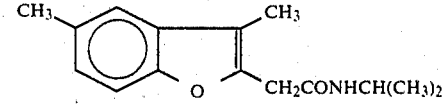

Melting point: 179°–180° C. (recrystallized from ethanol)

IR spectrum (KBr, tablet, cm$^{-1}$): 3280, 2975, 1650, 1470 1365, 795.

NMR spectrum (CDCl$_3$, δ value, ppm): 1.08(d, 6H), 2.17 (s, 3H), 2.47(s, 3H), 3.62(s, 2H), 3.70–4.30(m, 1H), 5.60(broad, 1H), 6.90–7.50(m, 3H).

Elemental analysis for C$_{15}$H$_{19}$NO$_2$:

|  | C (%) | H (%) | N (%) |
|---|---|---|---|
| Calculated: | 73.44 | 7.80 | 5.71 |
| Found: | 73.52 | 8.04 | 5.82 |

TABLE 1

| | List of the starting compounds used in Example 12 | | | | |
|---|---|---|---|---|---|
| End Compound | Starting Compound (II) (g) | SOCl$_2$ (ml) | Starting Compound (III) (ml) | Yield (g) | (%) |
| E | 3-Methyl-5-fluoro-benzo [b] furyl-2-acetic acid, 5.0 g | 10 | Methylamine, 10 ml (40% aqueous solution) | 4.7 | 88 |
| F | 3-Methyl-5-fluoro-benzo [b] furyl-2-acetic acid, 10.0 | 20 | Ethylamine, 12 | 10.1 | 89 |
| G | 3-Methyl-5-fluoro-benzo [b] furyl-2-acetic acid, 10.0 | 20 | n-Propylamine, 10 | 10.9 | 91 |
| H | 3-Methyl-5-fluoro-benzo [b] furyl-2-acetic acid, 10.0 | 20 | sec-Butylamine, 12 | 12.1 | 96 |
| I | 3-Methyl-5-fluoro-benzo [b] furyl-2-acetic acid, 5.0 | 10 | t-Butylamine, 10 | 5.3 | 84 |
| J | 3-Methyl-5-fluoro-benzo [b] furyl-2-acetic acid, 5.0 | 10 | Diethylamine, 10 | 5.3 | 84 |
| K | 3-Methyl-5-fluoro-benzo [b] furyl-2-acetic acid, 5.0 | 10 | Di-n-propylamine, 10 | 4.2 | 60 |
| L | 3-Methyl-5-fluoro-benzo [b] furyl-2-acetic acid, 5.0 g | 10 | Di-isopropylamine, 10 | 5.2 | 74 |
| M | 3-Methyl-5-fluoro-benzo [b] furyl-2-acetic acid, 5.0 | 10 | Di-n-butylamine, 10 | 7.5 | 98 |
| N | 3-Methyl-5-fluoro-benzo [b] furyl-2-acetic acid, 5.0 | 10 | Di-isobutylamine, 10 | 7.5 | 98 |
| O | 3-Methyl-5-fluoro-benzo [b] furyl-2-acetic acid, 5.0 | 10 | Methyl, n-butylamine, 10 | 5.7 | 86 |
| P | 3-Methyl-5-fluoro-benzo [b] furyl-2-acetic acid, 10.4 | 20 | Isopropylamine, 10 | 11.0 | 88 |
| Q | 3-Methyl-5-methoxy-benzo [b] furyl-2-acetic acid, 11.0 | 20 | Isopropylamine, 10 | 10.7 | 82 |
| R | 3-Methyl-5-phenyl-benzo [b] furyl-2-acetic acid, 13.3 | 20 | Isopropylamine, 10 | 13.2 | 86 |
| S | 3,5-Dimethylbenzo [b] furyl-2-acetic acid, 10.2 | 20 | Isopropylamine, 10 | 10.3 | 84 | an alkyl group having 1–4 carbon atoms wherein, when one of R$_2$ and R$_3$ represents a hydrogen atom, the other represents an alkyl group.

2. A compound according to claim 1, wherein R$_1$ is methyl, methoxy, phenyl or fluoro.

3. A compound according to claim 1 or 2 wherein R$_2$ and R$_3$ are methyl.

4. 2-Dimethylcarbamoylmethyl-3,5-dimethylbenzo[b]furan.

5. A muscle relaxant pharmaceutical composition containing, as the active ingredient, a muscle relaxant amount of the benzofuran derivative represented by the

What is claimed is:

1. A benzofuran derivative represented by the formula:

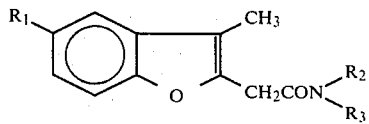

wherein R$_1$ represents an alkyl group having 1–4 carbon atoms, an alkoxy group having 1–4 carbon atoms, a phenyl group or a halogen atom, and R$_2$ and R$_3$ may be the same or different and represent a hydrogen atom or formula:

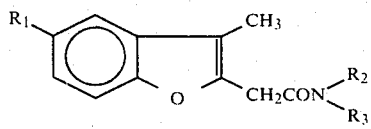

wherein R$_1$ represents an alkyl group having 1–4 carbon atoms, an alkoxy group having 1–4 carbon atoms, a phenyl group or a halogen atom, and R$_2$ and R$_3$ may be the same or different and represent a hydrogen atom or an alkyl group having 1–4 carbon atoms wherein, when one of $R_2$ and $R_3$ represents a hydrogen atom, the other represents an alkyl group, and at least one pharmaceutically acceptable carrier.

6. The composition according to claim 5, wherein $R_1$ is methyl, methoxy, phenyl or fluoro.

7. The composition according to claim 5 or 6 wherein $R_2$ and $R_3$ are methyl.

8. The composition according to claim 5, containing, as the active ingredient, a muscle relaxant amount of 2-dimethylcarbamoylmethyl-3,5-dimethylbenzo[b]furan.

* * * * *